(12) United States Patent
Haniu et al.

(10) Patent No.: US 6,475,328 B2
(45) Date of Patent: *Nov. 5, 2002

(54) ELECTRONIC COMPONENT MATERIAL CONTAINING PEST REPELLENT, ELECTRONIC COMPONENT USING THE SAME, AND ITS MANUFACTURING METHOD

(75) Inventors: Hirohiko Haniu, Moriguchi; Toshikazu Tomioka, Ibaraki; Katsumi Tomita, Katano; Susumu Kobayashi, Hirakata, all of (JP)

(73) Assignee: Matsushita Electric Industrial Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/455,648

(22) Filed: Dec. 7, 1999

(65) Prior Publication Data

US 2001/0055605 A1 Dec. 27, 2001

Related U.S. Application Data

(62) Division of application No. 09/015,365, filed on Jan. 29, 1998.

(30) Foreign Application Priority Data

Jan. 31, 1997 (JP) .............................................. 9-018117

(51) Int. Cl.⁷ .......................... A01N 25/00; B32B 31/00

(52) U.S. Cl. ................................ 156/307.3; 156/307.5; 156/307.7; 424/405; 424/411; 427/96

(58) Field of Search ................................. 424/405, 407, 424/409, 411, DIG. 10; 156/273.3, 275.5, 307.3, 307.5, 307.7; 427/508, 96, 385.5, 386; 522/170; 514/531, 532

(56) References Cited

U.S. PATENT DOCUMENTS

| | | | |
|---|---|---|---|
| 2,788,320 | A | 4/1957 | Bracey |
| 3,107,174 | A | 10/1963 | Wartman et al. |

(List continued on next page.)

FOREIGN PATENT DOCUMENTS

| | | |
|---|---|---|
| JP | 59227802 | 12/1984 |
| JP | 02020094 | 1/1990 |
| JP | 07112902 | 5/1995 |
| JP | 07118112 | 5/1995 |
| JP | 8-275713 | 10/1996 |
| JP | 8-275714 | 10/1996 |
| JP | 09007757 | 1/1997 |

OTHER PUBLICATIONS

European Search Report dated Jul. 27, 1998 for Int'l Appln No. 98101452.

*Primary Examiner*—Jeff H. Aftergut
(74) *Attorney, Agent, or Firm*—Ratner & Prestia

(57) ABSTRACT

To present printed wiring boards and other electronic components having excellent cockroach repelling performance even after solder reflow or solder flow. A conductive layer having a mounting land is provided on a insulating layer as a substrate, a solder resist is applied to cover the conductive layer excluding the mounting land, and an electronic component material containing a cockroach repellent is applied on the solder resist. This electronic component material is a paste containing a resin curable by crosslinking, a cockroach repellent, and a filler such as silica or talc, and by crosslinking and curing the resin by chemical reaction, a dried cockroach repelling layer is exposed and formed on the surface of the printed wiring board.

7 Claims, 3 Drawing Sheets

U.S. PATENT DOCUMENTS

| | | | |
|---|---|---|---|
| 3,864,468 A | | 2/1975 | Hyman et al. |
| 3,954,977 A | * | 5/1976 | Rife .............................. 514/66 |
| 3,989,610 A | * | 11/1976 | Tsukada et al. ............. 522/170 |
| 4,511,757 A | * | 4/1985 | Ors et al. ................... 174/258 |
| 4,530,992 A | | 7/1985 | Jones |
| 4,670,246 A | * | 6/1987 | Dahl et al. .................. 424/419 |
| 4,923,894 A | | 5/1990 | Kanda et al. |
| 5,023,247 A | | 6/1991 | Boulanger et al. |
| 5,229,252 A | * | 7/1993 | Flynn et al. ................. 522/170 |
| 5,400,221 A | | 3/1995 | Kawaguchi |

* cited by examiner

ELECTRONIC COMPONENT MATERIAL CONTAINING PEST REPELLENT, ELECTRONIC COMPONENT USING THE SAME, AND ITS MANUFACTURING METHOD

This application is a division of U.S. patent application Ser. No. 09/015,365, filed Jan. 29, 1998.

TECHNICAL FIELD OF THE INVENTION

The present invention relates to an electronic component material containing pest repellent effective for repelling pest insects in electronic appliances used in professional kitchen and food industry, that is, electronic appliances of which reliability may be spoiled by pest insects, and electronic components using the same.

BACKGROUND OF THE INVENTION

Hitherto, environments inhabited excessively by cockroaches and other harmful insects were not assumed, and it was very rare to encounter trouble of electronic appliance due to dead bodies and excrement of insects. Accordingly, pest control measures were not taken within the electronic appliances, but the pest control measures were applied in the entire environments.

However, as the electronic appliances are diversified, and the restaurant industry is grown widely, there is a mounting demand for reliability of electronic appliances used in professional kitchens and food industry (for example, electric cooking tools and kitchen telephones), and the pest control measures are needed in the electronic appliances themselves.

For example, a conventional cockroach repellent was applied in necessary places by adhering, coating, or placing. If the conventional cockroach repel lent is directly used in the members of electronic components, it is evaporated and decomposed in the manufacturing process of electronic appliances due to heat load of solder reflow or solder flow. Therefore, the cockroach repellent cannot be directly used in the printed wiring board. On the other hand, the technique for applying a mixed material of resin and cockroach repellent after fabricating the printed wiring board through heat load process was proposed, for example, in Japanese Laid-open Patent No. 8-275713 and Japanese Laid-open Patent No. 8-275714. These prior arts disclose the packing material or sealing material by molding a silicone resin containing an absorbent absorbing a cockroach repellent and a bleed-out agent into a specified shape, and the molded material is put in the appliance. In these prior arts, moreover, a paint composed of a cockroach repellent and a urethane resin dissolved in thinner is applied on the appliance, and the coat film drying the paint is presented. However, when such prior arts are applied in the printed wiring board and electronic component, the adhesion of the cockroach repellent which is the minimum limit of reliability of such printed wiring board and electronic component cannot be maintained, and further it was complicated and difficult in the manufacturing process of electronic appliances to apply such conventional resin after the heat load process of mounting components.

In the case of the printed wiring board using such conventional cockroach repellent, at the maximum reaching temperature of 240° C. of the solder reflow or solder flow temperature of 250° C. (set temperature of solder bath), the cockroach repellent is partly evaporated and decomposed, and when the performance of cockroach repellent deteriorates significantly. Besides, after similar heat load, the adhesion of the cockroach repellent on the printed wiring board and electronic component cannot be guaranteed.

It is hence an object of the invention to present an electronic component material containing pest repellent having a pest control effect even after solder reflow and solder flow and capable of assuring reliability and adhesion when used in electronic appliances, and an electronic component using the same.

SUMMARY OF THE INVENTION

An electronic component material of the invention comprises a resin which can be crosslinked and cured, a pest repellent contained in the resin, and a filler contained in the resin, in which a pest repelling layer is formed by curing the resin by crosslinking chemical reaction.

In this constitution, by forming the pest repelling layer containing the filler, the pest repelling layer does not deteriorate at all even after heat load of high temperature when manufacturing electronic appliances such as printed wiring boards, and the pest repelling layer maintaining an excellent stress relaxation and superior adhesion is obtained. Moreover, in the cleaning process by solvent after soldering, the pest repelling layer and the pest repellent are not impaired by the solvent.

Preferably, the curable resin contains epoxy resin and hardener.

Preferably, the curable resin contains epoxy acrylate, reactive diluent and light initiator. In this constitution, when applied in an electronic component, the adhesion of the pest repelling layer is further enhanced, and when cleaning at high temperature in the soldering process, the pest repelling layer having an excellent pest repelling effect is obtained. Further, when curing, part of the pest repellent is moved to the surface of the pest repelling layer, and is dispersed in the entire area, and the repelling effect of cockroaches and other insects is extremely exhibited.

An electronic component of the invention comprises:

(a) a printed wiring board having an electric insulating board and a conducive layer disposed on the surface of the electric insulating board, and (b) a pest repelling layer disposed on the surface of the printed wiring board, in which the pest repelling layer contains a crosslinked and cured resin, and a pest repellent dispersed and disposed in the resin. The pest repelling layer also functions as an electric insulating layer.

In this constitution, the printed wiring board remarkably exhibiting the effects of repelling cockroaches and other insects is obtained. At the same time, since the pest repellent is fixed by the resin which is crosslinked and cured, when soldering other electronic components on the printed wiring board by high temperature solder, melting of resin and deterioration of pest repellent can be prevented, and the printed wiring board maintaining an excellent pest repelling effect against soldering is obtained. Moreover, after high temperature heat load and cleaning process in manufacture of printed wiring board, the pest repelling layer maintaining an excel lent stress relaxation and superior adhesion is obtained.

A manufacturing method of electronic component of the invention is a manufacturing method of electronic component having a pest repelling layer with a performance of repelling pest insects on the surface of a printed wiring board.

The method comprises:

(a) a step of adjusting an electronic component material having a pest repellent and a resin which can be crosslinked and cured, (b) a step of applying the electronic component material at a specified position on the surface of the printed wiring board, and (c) a step of forming the cured pest repelling layer, containing the pest repellent, by crosslinking chemical reaction of the resin in the electronic component material on the printed wiring board.

According to this method, even after heat load or in cleaning process in manufacture of printed wiring board, the pest repelling layer having an excellent stress relaxation and superior adhesion is obtained. Moreover, the printed wiring board remarkably exhibiting the effects of repelling cockroaches and other pests can be manufactured at low cost. At the same time, since the since the pest repellent is fixed in the crosslinked and cured resin, when soldering other electronic components on the printed wiring board by high temperature solder, melting of resin and deterioration of pest repellent can be prevented, and the printed wiring board maintaining an excellent pest repelling performance even against soldering is obtained.

In this constitution, preferably, the electronic component material further contains a filler. The pest repelling layer further contains a filler.

By containing the filler, the mechanical strength of the pest repelling layer is improved, and the stress relaxation is enhanced, and the adhesion is further increased. Furthermore, the pest repellent is adsorbed on the filler such as silica or talc, and the filler component contributes to enhance the dispersion of the pest repellent.

REFERENCE NUMERALS

Figure 1:
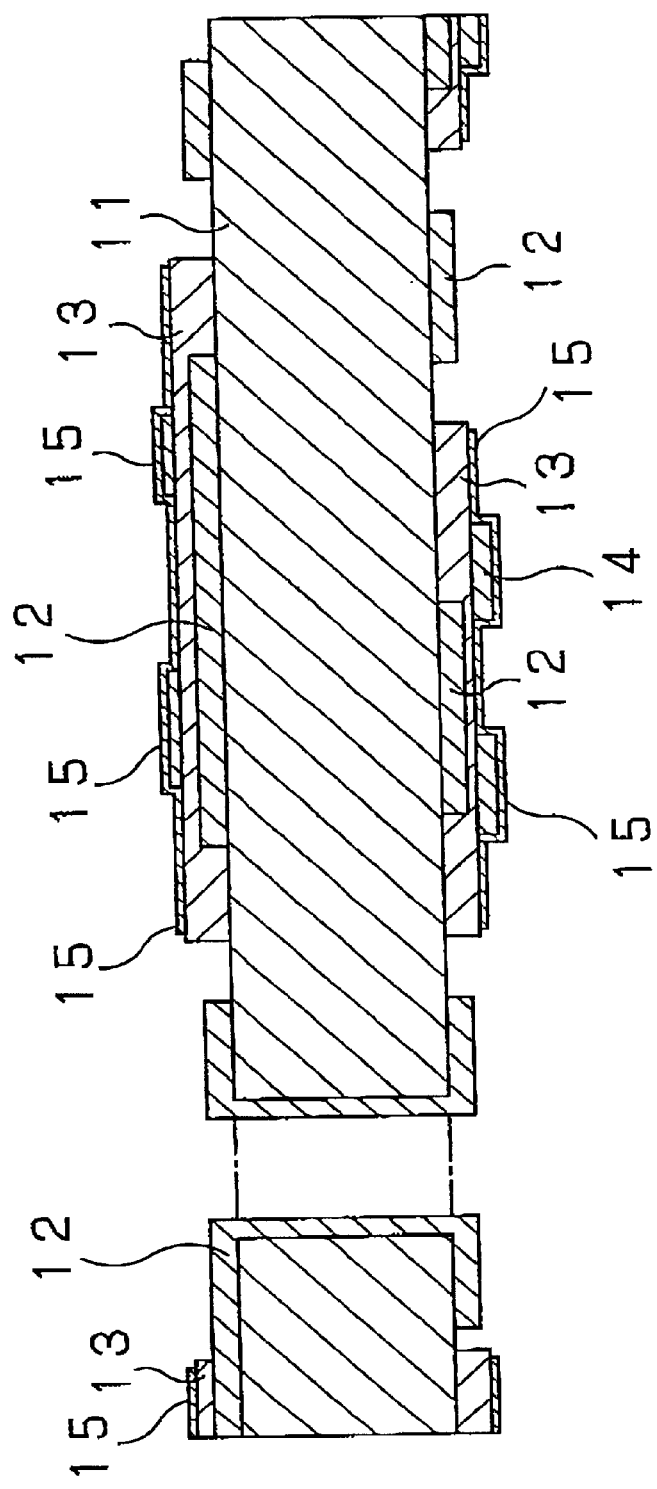
FIG. 1 is a sectional view of essential parts showing an embodiment of a printed wiring board of the invention.

11 Insulating layer (substrate)
12 Conductive layer
13 Solder resist
14 Road map (parts layout)
15 Cockroach repelling paste
21 Insulating layer (substrate)
22 Conductive layer
23 Solder resist containing cockroach repellent
24 Road map (parts layout)
31 Insulating layer (inner layer base material)
32 Insulating layer containing cockroach repellent
33 Conductive layer
34 Solder resist
35 Road map (parts layout)

The entire disclosure of U.S. patent application Ser. No. 09/015,365, filed Jan. 29, 1998 is expressly incorporated by reference herein.

DETAILED DESCRIPTION OF THE INVENTION

An electronic component material in an embodiment of the invention comprises an epoxy resin, a hardener, a reaction promoter, a solvent, a cockroach repellent, and a filler such as silica or talc, being a paste containing 5 to 150 parts by weight of the cockroach repellent in 100 parts by weight of the epoxy resin. By containing the solvent, when forming a coat film of the paste (by printing, curing, etc.) the cockroach repellent is dispersed in the entire paste, and the cockroach repelling performance is exhibited. When disposed on the surface of the printed wiring board, since the epoxy resin is used, the adhesion with the substrate is notably improved. Further, at high temperature when soldering, for example, the resin and cockroach repellent do not deteriorate, and an excellent cockroach repelling performance is maintained. Also, even in the cleaning process by solvent after soldering, the resin and cockroach repellent do not deteriorate, and an excellent cockroach repelling performance is maintained.

An electronic component material in other embodiment of the invention comprises epoxy acrylate, a reactive diluent, a light initiator, a cockroach repellent, and a filler such as silica or talc, being a paste containing 2 to 100 parts by weight of the cockroach repellent in 100 parts by weight of the epoxy acrylate. When forming a coat film of the paste (by printing, curing, etc.), at the time of curing of the epoxy acrylate, the cockroach repellent is cured and dried on the coat film surface in a floating state. Therefore, if the content of the cockroach repellent is small, the cockroach repellent is much dispersed on the surface layer which contacts with the antennae of cockroaches, so that a sufficient cockroach repelling performance is exhibited. Further, after heat load at high temperature when soldering and cleaning process, an excellent cockroach repelling performance is maintained.

An electronic component material in a different embodiment of the invention comprises an epoxy resin, a reactive diluent, a light initiator, a hardener, a reaction promoter, a solvent, a cockroach repellent, and a filler such as silica or talc, being a paste containing 5 to 100 parts by weight of the cockroach repellent in 100 parts by weight of the epoxy resin. By containing the solvent, when temporarily drying and curing the coat film of the paste, part of the cockroach repellent is dispersed in the entire paste, and the cockroach repelling performance is exhibited. At the same time, when exposing the coat film of the paste (curing by ultraviolet ray), the cockroach repellent is excluded from the curing mechanism of epoxy acrylate, and hence part of the cockroach repellent floats up on the surface of the coat film of the paste, and if the content of the cockroach repellent is small, the cockroach repellent is much dispersed on the surface layer which contacts with the antennae of cockroaches, so that a sufficient cockroach repelling performance is exhibited. Further, after heat load at high temperature when soldering and cleaning process, an excellent cockroach repelling performance is maintained.

An electronic component material in a further different embodiment of the invention comprises an epoxy resin, a hardener, a reaction promoter, a solvent, a cockroach repellent, a filler such as silica or talc, and a coloring pigment such as titanium oxide, being a paste containing 5 to 150 parts by weight of the cockroach repellent in 100 parts by weight of the epoxy resin. By containing the solvent, when forming a coat film of the paste (by printing, curing, etc.), the cockroach repellent is dispersed in the entire paste, and the cockroach repelling performance is exhibited. At the same time, the paste also acts as the ink for drawing parts layout of printed wiring board or the like, and ink for printing characters. Further, after heat load at high temperature when soldering and cleaning process, an excellent cockroach repelling performance is maintained.

An electronic component material in a further different embodiment of the invention comprises an epoxy resin, a hardener, a reaction promoter, a solvent, a cockroach repellent, a filler such as silica or talc, and a coloring pigment such as phthalocyanine green, being a solder resist containing 8 to 120 parts by weight of the cockroach repellent in 100 parts by weight of the epoxy resin. In the form of solder resist, the insulation of the conductive layer is maintained and the conductive circuit layer is protected from soldering, and by containing the solvent, when forming a coat film of the solder resist (by printing, curing, etc.), the cockroach repel lent is dispersed in the entire solder resist, and the cockroach repelling performance is exhibited. Further, after heat load at high temperature when soldering and cleaning process, an excellent cockroach repelling performance is maintained.

An electronic component material in a further different embodiment of the invention comprises epoxy acrylate, a reactive diluent, a light initiator, a cockroach repellent, a filler such as silica or talc, and a coloring pigment such as phthalocyanine green, being a solder resist containing 5 to 80 parts by weight of the cockroach repellent in 100 parts by weight of the main ingredient of epoxy acrylate. In the form of solder resist, the insulation of the conductive layer is maintained, and the conductive circuit layer is protected when soldering. At the same time, when forming a coat film of the solder resist (by printing, curing, etc.), the cockroach repellent is excluded from the curing mechanism of the main ingredient of epoxy acrylate, and hence part of the cockroach repellent floats up on the surface of the coat film of the solder resist, and if the content of the cockroach repel lent is small, the cockroach repellent is much dispersed on the surface layer which contacts with the antennae of cockroaches, so that a sufficient cockroach repelling performance is exhibited. Further, after heat load at high temperature when soldering and cleaning process, an excellent cockroach repelling performance is maintained.

An electronic component material in a further different embodiment of the invention comprises an epoxy resin, a reactive diluent, a light initiator, a hardener, a reaction promoter, a solvent, a cockroach repellent, a filler such as silica or talc, and a coloring pigment such as phthalocyanine green, being a solder resist containing 10 to 80 parts by weight of the cockroach repellent in 100 parts by weight of the main ingredient of epoxy resin. In the form of solder resist, the insulation of the conductive layer is maintained, and the conductive circuit layer is protected from soldering, and by containing the solvent, when temporarily drying and curing the coat film of the solder resist, part of the cockroach repellent is dispersed in the entire solder resist and the cockroach repelling performance is exhibited. Moreover, when exposing the coat film of the solder resist (by ultraviolet ray curing), the cockroach repellent is excluded from the curing mechanism of epoxy acrylate, and hence part of the cockroach repellent floats up on the surface of the coat film of the solder resist, and if the content of the cockroach repellent is small, the cockroach repellent is much dispersed on the surface layer which contacts with the antennae of cockroaches, so that a sufficient cockroach repelling performance is exhibited. Further, after heat load at high temperature when soldering and cleaning process, an excellent cockroach repelling performance is maintained.

An electronic component material in a further different embodiment of the invention is composed by impregnating and temporarily drying varnish mainly comprising an epoxy resin, a hardener, a reaction promoter, a solvent, and a cockroach repellent in E type glass cloth (woven fabric) or glass non-woven fabric or paper, being a prepreg containing 10 to 80 parts by weight of the cockroach repellent in 100 parts by weight of the epoxy resin. By containing the solvent, when temporarily drying the prepreg, the cockroach repel lent is dispersed in the entire insulating layer of the prepreg, and the cockroach repelling performance is exhibited uniformly in the plane of the printed wiring board. At the same time, by using the prepreg, the main object of the cockroach repelling performance of the invention may be applied to the base material for the printed wiring board in all layer compositions. Further, after heat load at high temperature when soldering and cleaning process, an excellent cockroach repelling performance is maintained.

An electronic component material in a further different embodiment of the invention comprises an epoxy resin, a hardener, a reaction promoter, a solvent, and a cockroach repellent, being an insulating layer resin containing 10 to 80 parts by weight of the cockroach repellent in 100 parts by weight of the main ingredient of epoxy resin. By containing the solvent, when temporarily drying the insulating layer resin containing the cockroach repellent, the cockroach repel lent is dispersed in the entire insulating layer resin, and the cockroach repelling performance is exhibited uniformly in the plane of the printed wiring board. At the same time, by using the insulating layer resin, the main object of the cockroach repelling performance of the invention may be applied to the base material for the printed wiring board in all layer compositions. Further, after heat load at high temperature when soldering and cleaning process, an excellent cockroach repelling performance is maintained.

An electronic component material in a further different embodiment of the invention comprises an epoxy resin, a hardener, a reaction promoter, and a cockroach repellent, being a thermosetting resin film containing 10 to 80 parts by weight of the cockroach repellent in 100 parts by weight of the epoxy resin. The insulating resin film containing the cockroach repellent is fabricated (by temporarily drying the film), and by containing the solvent, the cockroach repellent is dispersed in the entire resin film, and the cockroach repelling performance is exhibited uniformly in the plane of the printed wiring board. At the same time, by using the resin film, the main object of the cockroach repelling performance of the invention may be applied to the base material for the printed wiring board in all layer compositions. Further, after heat load at high temperature when soldering and cleaning process, an excellent cockroach repelling performance is maintained.

An electronic component material in a further different embodiment of the invention is characterized by using a neurotransmitter repellent of pyrolysis temperature of 250° C. or more as cockroach repellent. The neurotransmitter repellent acts by making use of skin stimulation when contacting with antennae and forelegs of cockroaches when cockroaches invade. Further, after heat load at high temperature when soldering, an excellent cockroach repelling performance is maintained.

An electronic component material in a further different embodiment of the invention is characterized by using a pyrethroid compound as a neurotransmitter repellent. The printed wiring board and electronic component coated with this cockroach repellent is applied in electric products used in living environments and food handling industry. By using the pyrethroid compound, even in the material low in the vapor pressure, is evaporating from the printed wiring board or electronic component, safety of human body and low level of environmental contamination are assured, and safety and environmental safety are maintained. Further, after heat load at high temperature when soldering and cleaning process, an excellent cockroach repelling performance is maintained.

An electronic component in an embodiment of the invention comprises a conductive layer disposed on an insulating layer, and a pest repelling layer disposed so as to cover the conductive layer. As the pest repelling layer, a layer is composed by crosslinking and curing various electronic component materials mentioned above. As the conductive layer, a mounting land is formed, and the pest repelling layer is disposed to cover the position excluding the mounting land. As such electronic component, a printed wiring board is preferred.

Alternatively, covering the conductive layer, a solder resist is disposed, and the pest repelling layer may be disposed on the solder resist.

In such constitution, when a cockroach is about to get into the electronic appliance by heat attraction or diet attraction, the moment an antenna of the cockroach contacts with the printed wiring board, invasion of the cockroach into the electronic appliance is prevented by the pest repelling layer disposed in the printed wiring board. Moreover, the pest repelling layer is strongly adhered to the conductive layer, solder resist, and insulating layer, and the adhesion performance is notably enhanced. Furthermore, at high temperature when soldering, etc., the resin and pest repellent do not deteriorate, and an excellent pest repelling performance is maintained. Also in the cleaning process by solvent after soldering, the resin and pest repellent do not deteriorate, and an excellent pest repelling performance is maintained.

Preferably, the electronic component contains a filler. By containing the filler, even after heat load of high temperature when manufacturing the electronic appliance, an excellent stress relaxation and a superior adhesion are obtained. Further, the cockroach repellent is adsorbed on the filler such as silica, and this filler component enhances the dispersion of the cockroach repellent. When a cockroach is about to get into the electronic appliance by heat attraction or diet attraction, the moment an antenna of the cockroach contacts with the printed wiring board thus constituted in the embodiment, invasion of the cockroach into the electronic appliance is prevented by the pest repelling layer disposed in the printed wiring board.

An electronic component in other embodiment of the invention comprises a pest repelling layer placed in a width of 10 cm or more, in the outer peripheral region of the printed wiring board further in the above electronic component. When a cockroach is about to get into the electronic appliance by heat attraction or diet attraction, the moment an antenna of the cockroach contacts with the printed wiring board (contacting with the cockroach repellent applied in a range over 10 cm exceeding the body length of the cockroach in the outer periphery of the printing wiring board), invasion of the cockroach into the electronic appliance is prevented by the pest repelling layer disposed in the outer peripheral region of the printed wiring board. Further, after heat load at high temperature when soldering and cleaning process, an excellent cockroach repelling performance is maintained.

An electronic component in a different embodiment of the invention is a two-sided or one-sided printed wiring board manufactured in (a) a step of laminating a prepreg containing the above pest repellent, and a copper foil in a circuit shape, pressing and heating, and fabricating a printed wiring board having a copper clad circuit layer and a pest repelling layer, and (b) a step of covering the copper clad circuit layer with a solder resist. In this constitution, the consumption of the solder resist can be saved. Moreover, by containing a solvent, when curing the copper clad layer by pressing and heating, the pest repellent is disposed on the surface of the pest repelling layer, so that the cockroach repelling performance is exhibited. Further, after heat load at high temperature when soldering and cleaning process, an excellent cockroach repelling performance is maintained.

An electronic component in a further different embodiment of the invention is a multilayer printed wiring board manufactured in (a) a step of inserting a copper foil circuit board for an inner layer conductive circuit layer between a glass-epoxy substrate having an outer layer conductive circuit layer and a prepreg containing a pest repellent (a prepreg of glass-epoxy), and pressing and heating to fabricate a laminate, and (b) a step of covering the outer layer circuit layer with a solder resist. That is, on the surface of the multilayer printed wiring board fabricated in this method, the pest repelling layer containing the pest repellent is disposed, and this pest repelling layer functions also as an electric insulating layer. In this constitution, the consumption of the solder resist can be saved. Moreover, by containing a solvent, when curing the copper clad layer by pressing and heating, the pest repellent is dispersed in the entire insulating layer of the laminate, and the pest repelling layer is exposed, and the laminate is formed. As a result, the electronic component having an excellent pest repelling performance is obtained. Further, after heat load at high temperature when soldering and cleaning process, an excellent cockroach repelling performance is maintained.

An electronic component in a further different embodiment of the invention is a multilayer printed wiring board further having an IVH (interstitial via hole) in the above multilayer printed wiring board. In this constitution, the multilayer printed wiring board having the IVH (interstitial via hole) having the same effects above is obtained.

An electronic component in a further different embodiment of the invention is a multilayer printed wiring board manufactured in (a) a step of placing an inner layer conductive circuit layer on the surface of an insulating layer of a glass-epoxy resin, (b) a step of covering the inner layer conductive circuit layer, adhering an electronic component material containing the above pest repellent, and forming a pest repelling layer by using a resin, (c) a step of disposing an outer layer conductive circuit layer on the surface of the other side of the insulating layer, and (d) a step of applying a solder resist in the region of the outer layer conductive layer excluding the mounting land. At step (b), the electronic component material is applied by screen printing, curtain coating or laminating method. In this constitution, the consumption of the solder resist can be saved. Moreover, by containing a solvent, when curing the electronic component material, the pest repellent is dispersed in the entire pest repelling layer, and the pest repelling layer is exposed, and the multilayer printed wiring board is formed. As a result, the electronic component having an excellent pest repelling performance is obtained. Further, after heat load at high temperature when soldering and cleaning process, an excellent cockroach repelling performance is maintained.

An electronic component in a further different embodiment of the invention is a multilayer printed wiring board manufactured in (a) a step of placing an inner layer conductive circuit layer on the surface of an insulating layer of a glass-epoxy resin, (b) a step of covering the inner layer conductive circuit layer, and laminating a film containing the above pest repellent to form a pest repelling layer, and (c) a step of laminating and placing an outer layer conductive circuit layer on the surface of the other side of the insulating layer.

An electronic component in a further different embodiment of the invention is a multi layer printed wiring board manufactured in (a) a step of placing an inner layer conductive circuit layer on the surface of an insulating layer of a glass-epoxy resin, (b) a step of covering the inner layer conductive circuit layer, and laminating a film containing the above pest repellent, (c) a step of laminating an outer layer conductive circuit layer on the surface of the other side of the insulating layer, (d) a step of pressing and heating a laminate of the laminated insulating layer, inner layer conductive circuit layer, film layer and outer layer circuit layer, and (e) a step of placing a solder resist to cover the outer layer conductive circuit excluding the mounting land. In this constitution, the consumption of the solder resist can be saved. Moreover, by containing a solvent, when curing the copper clad layer by pressing and heating, the pest repellent is dispersed in the entire insulating layer of the laminate, and the pest repelling layer is exposed, and the laminate is formed. As a result, the electronic component having an excellent pest repelling performance is obtained. Further, after heat load at high temperature when soldering and cleaning process, an excellent cockroach repelling performance is maintained.

An electronic component in a further different embodiment of the invention is an electronic component forming a pest repelling layer on the top of an electronic component such as IC or LSI, by applying a paste containing a resin which can be crosslinked and cured, a pest repellent, and a filler such as silica or talc. In this constitution, after heat load when manufacturing the electronic appliance, an excellent stress relaxation and adhesion can be obtained. In particular, the IC or LSI is at a temperature suitable to inhabitation of cockroaches, and when a cockroach is about to get into the electronic appliance by heat attraction or diet attraction, if an antenna of the cockroach contacts with the pest repellent contained in the electronic component, invasion of the cockroach into the electronic appliance is prevented. Further, after heat load at high temperature when soldering and cleaning process, an excellent cockroach repelling performance is maintained.

An electronic component in a further different embodiment of the invention is constituted by applying a paste containing a resin which can be crosslinked and cured, a pest repellent, a filler such as silica or talc, and a coloring pigment such as titanium oxide, on the top of an electronic component such as IC or LSI, and forming the manufacturer's name or product number in stencil characters or graphic patterns (characters or patterns exposing the background color of the top of the electronic component without printing), thereby disposing a pest repelling layer. In this constitution, the same effects as above are exhibited, and also the manufacturer's name or product name of the electronic component can be displayed at the same time.

DESCRIPTION OF THE PREFERRED EMBODIMENTS

In the electronic component material in the embodiments of the invention, the pest repellent is a neurotransmitter pest repellent of which pyrolysis temperature is at least 250° C. or more. As such repellent, for example, at least a pyrethroid compound is used. As the electronic component material, the following materials are used.

(a) A thermosetting paste mainly comprising principal ingredient epoxy resin, hardener, reaction promoter, solvent, and cockroach repellent, being a paste containing cockroach repellent containing 100 parts by weight of principal ingredient epoxy resin, 5 to 150 parts by weight of cockroach repellent, and filler such as silica or talc, (b) An ultraviolet curing paste mainly comprising principal ingredient epoxy acrylate, reactive diluent, light initiator, and cockroach repellent, being a paste containing cockroach repellent containing 100 parts by weight of principal ingredient epoxy acrylate, 2 to 100 parts by weight of cockroach repellent, and filler such as silica or talc, (c) A paste for exposure development of dual curing (ultraviolet curing+thermosetting) type mainly comprising principal ingredient epoxy resin, reactive diluent, light initiator, hardener, reaction promoter, solvent, and cockroach repellent, being a paste containing cockroach repellent containing 100 parts by weight of principal ingredient epoxy resin, 5 to 100 parts by weight of cockroach repellent, and filler such as silica or talc, (d) A thermosetting paste mainly comprising principal ingredient epoxy resin, hardener, reaction promoter, solvent, and cockroach repellent, being a paste containing cockroach repellent containing 100 parts by weight of principal ingredient epoxy resin, 5 to 150 parts by weight of cockroach repellent, filler such as silica or talc, and coloring pigment such as titanium oxide, (e) A thermosetting solder resist mainly comprising principal ingredient epoxy resin, hardener, reaction promoter, coloring pigment, solvent, and cockroach repellent, being a solder resist containing cockroach repellent containing 100 parts by weight of principal ingredient epoxy resin, 8 to 120 parts by weight of cockroach repellent, and filler such as silica or talc, (f) An ultraviolet curing solder resist mainly comprising principal ingredient epoxy acrylate, reactive diluent, light initiator, coloring pigment, and cockroach repellent, being a solder resist containing cockroach repellent containing 100 parts by weight of principal ingredient epoxy acrylate, 5 to 80 parts by weight of cockroach repellent, and filler such as silica or talc, (g) A solder resist (photo resist) for exposure development of dual curing (ultraviolet curing+thermosetting) type mainly comprising principal ingredient epoxy resin, reactive diluent, light initiator, hardener, reaction promoter, coloring pigment, solvent, and cockroach repellent, being a solder resist containing cockroach repellent containing 100 parts by weight of principal ingredient epoxy resin, 10 to 80 parts by weight of cockroach repellent, and filler such as silica or talc, (h) A prepreg impregnating and temporarily drying a varnish mainly comprising principal ingredient epoxy resin, hardener, reaction promoter, solvent, and cockroach repellent in E type glass cloth or glass nonwoven fabric or paper, being a prepreg containing cockroach repellent containing 100 parts by weight of principal ingredient epoxy resin, and 10 to 80 parts by weight of cockroach repellent, (i) A thermosetting resin mainly comprising principal ingredient epoxy resin, hardener, reaction promoter, solvent, and cockroach repellent, being an insulating layer resin containing cockroach repellent containing 100 parts by weight of principal ingredient epoxy resin, 10 to 80 parts by weight of cockroach repellent, and filler such as silica or talc, and (j) A thermosetting resin film mainly comprising principal ingredient epoxy resin, hardener, reaction promoter, and cockroach repellent, being a copper foil with an insulating layer resin containing cockroach repellent containing 100 parts by weight of principal ingredient epoxy resin, and 10 to 80 parts by weight of cockroach repellent.

The content of the filler contained in each one of the above electronic component materials is preferred to be 2 to 150 parts by weight. If out of this range, the effects for enhancing the mechanical strength and adhesion of the pest repelling layer are slightly lowered.

The printed wiring board using the electronic component material containing cockroach repellent in the embodiments of the invention is composed as follows.

(a) A printed wiring board comprising a conductive layer disposed on an insulating layer, a solder resist disposed to cover the conductive layer except for the mounting land for soldering, and a cockroach repelling layer disposed to cover the solder resist, (b) A printed wiring board comprising a conductive layer disposed on an insulating layer, and a solder resist containing cockroach repel lent disposed to cover the conductive layer except for the mounting land for soldering, (c) A printed wiring board comprising a conductive layer disposed on an insulating layer, a solder resist disposed to cover the conductive layer except for the mounting land for soldering, a parts layout containing a coloring pigment and a cockroach repellent disposed to cover the solder resist, and a pest repelling layer disposed in the outer periphery, (d) A two-sided or one-sided printed wiring board formed by heating and pressing a prepreg containing cockroach repellent and a copper foil for forming a conductive circuit to manufacture a laminate, and covering the conductive layer except for mounting land of the conductive circuit with a solder resist, (e) A multilayer printed wiring board comprising a laminate having an insulating layer of ordinary glass-epoxy resin and a copper clad circuit for inner layer disposed on the surface of the insulating layer, a copper clad circuit for outer layer disposed between it and a prepreg containing a cockroach repellent, and a solder resist disposed in a circuit except for the mounting land of the copper clad circuit for outer layer, and (f) A multilayer printed wiring board having IVH in the above multilayer printed wiring board.

The insulating layer containing the cockroach repellent disposed in the outermost layer of the above printed wiring boards is exposed.

In such constitution, circuit elements are disposed on the printed wiring board. The circuit elements are slightly heated by energization. Since the growth speed of cockroach depends on the ambient temperature, the cockroach is attracted to the atmosphere of 27±5° C. The circuit elements on the printed wiring board are heated to this temperature range, and the cockroach is likely to inhabit this surface. When getting into the printed wiring board, the cockroach has a habit of searching by its antennae and forelegs, and hence the cockroach is likely to contact with the repellent applied on the surface of the printed wiring board.

The surface of antenna of cockroach has a cuticular structure, which is different from the human dermal structure. The cockroach repellent is preferred to be a neurotransmitter having a property of stimulating through the skin of the cockroach. The neurotransmitter is harmless for the human, and repels only the cockroach. The neurotransmitter, unlike the olfactory stimulating compound, is not required to raise the vapor pressure of the compound. Accordingly, useless volatile dissipation of the compound is suppressed, and the performance is retained for a long period. Moreover, by the learning effect of cockroach, by repeating this repelling action several times, it is expected that nest building may be given up.

The repellent is preferred to be a material having pyrolysis temperature of 250° C. or more. By using the repellent having the pyrolysis temperature of 250° C. or more, the printed wiring board undergoing a soldering process is not adversely affected by high temperature of soldering. Moreover, in the cleaning process by the solvent after soldering, an excellent cockroach repelling performance is maintained.

As the electronic component, the following electronic components may be also used.

(a) An electronic component formed by applying a paste containing the cockroach repellent on the top surface of an electronic component such as IC or LSI (the electronic component mounting side being the lower side), and (b) An electronic component by applying a paste containing cockroach repellent, containing cockroach repellent, filler such as silica or talc, and coloring pigment such as titanium oxide, on the top surface of an electronic component such as IC or LSI (the electronic component mounting side being the lower side), and forming the manufacturer's name or product number in stencil characters or graphic patterns (characters or patterns exposing the background color of the top of the electronic component without printing).

In this constitution of the invention, lowering of reliability of the electronic appliance due to invasion of cockroaches can be prevented. Moreover, when the resin member containing the neurotransmitter repellent is used in the electronic component such as printed wiring board, IC and LSI, lowering of reliability due to invasion of ants and other insects can be prevented.

Referring now to the accompanying drawings, embodiments of the invention are more specifically described below.

FIG. 1 shows a sectional view of essential parts of a two-sided copper through-hole printed wiring board in an embodiment of the invention. In FIG. 1, reference numeral 11 is a glass-epoxy (FR-4) insulating layer (substrate). Reference numeral 12 is a conductive layer having a 25 $\mu$m copper plating applied on an 18 $\mu$m thick copper foil. Reference numeral 13 is an ultraviolet curing type solder resist. Reference numeral 14 is an ultraviolet curing type road map (parts layout). Reference numeral 15 is an electronic component material containing cockroach repellent. This electronic component material containing cockroach repellent 15 is formed by curing an ultraviolet curing type paste containing 100 parts by weight of principal ingredient epoxy acrylate, 30 parts by weight of methacrylic acid monomer as reactive diluent, 3 parts by weight of benzoin as light initiator, 2 parts by weight of peroxyl ester as peroxide catalyst, 60 parts by weight of talc and 5 parts by weight of silica as filler, and 50 parts by weight of neurotransmitter cockroach repellent of pyrethroid derivative with the minimum heat resisting temperature of pyrolysis temperature or the like of 264° C.

Figure 2:
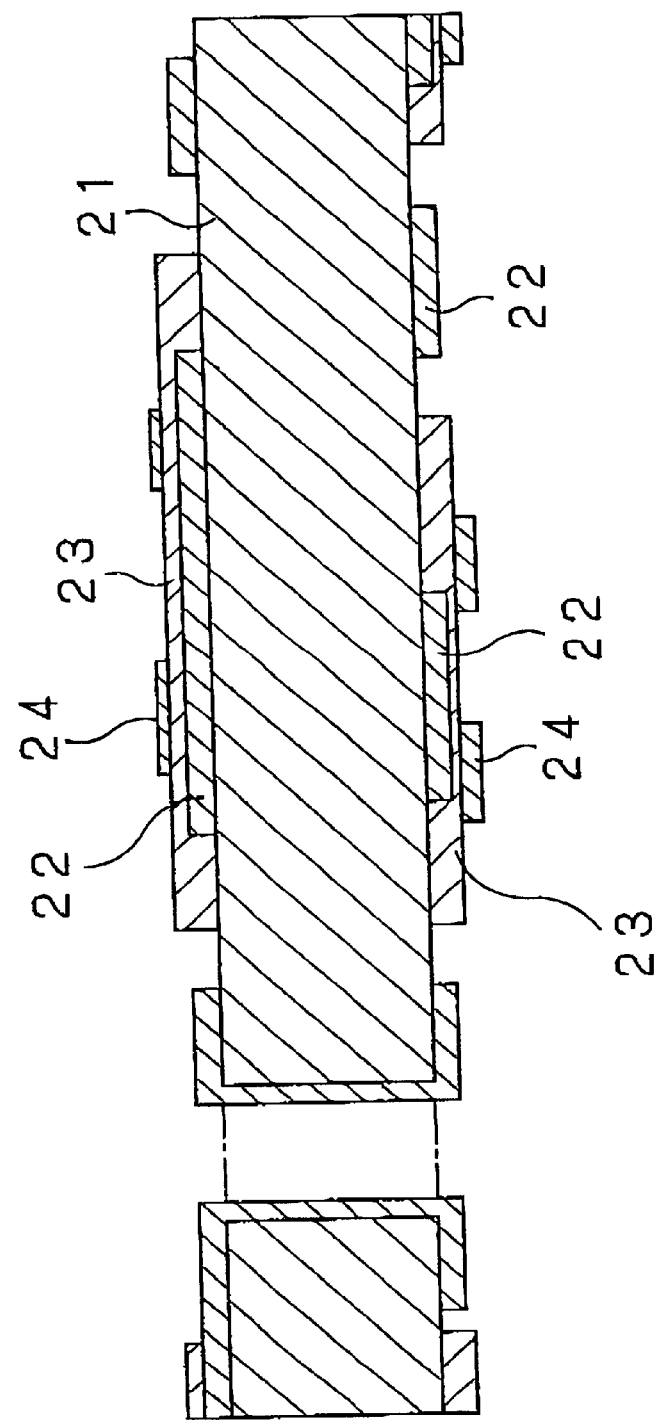
FIG. 2 is a sectional view of essential parts showing other embodiment of a printed wiring board of the invention.

FIG. 2 shows a sectional view of essential parts of a two-sided copper through-hole printed wiring board in other embodiment of the invention. In FIG. 2, reference numeral 21 is a glass-epoxy (FR-4) insulating layer (substrate).

Reference numeral 22 is a conductive layer having a 25 μm copper plating applied on an 18 μm thick copper foil. Reference numeral 23 is an electronic component material containing cockroach repellent. This electronic component material containing cockroach repellent 23 is formed by curing an ultraviolet curing type solder resist containing 100 parts by weight of principal ingredient epoxy acrylate, 30 parts by weight of methacrylic acid monomer as reactive diluent, 3 parts by weight of benzoin as light initiator, 2 parts by weight of peroxyl ester as peroxide catalyst, 1.5 parts by weight of phthalocyanine green as coloring pigment, 58 parts by weight of talc and 5 parts by weight of silica as filler, and 50 parts by weight of neurotransmitter cockroach repellent of pyrethroid derivative. Reference numeral 24 is an ultraviolet curing type road map (parts layout).

Figure 3:
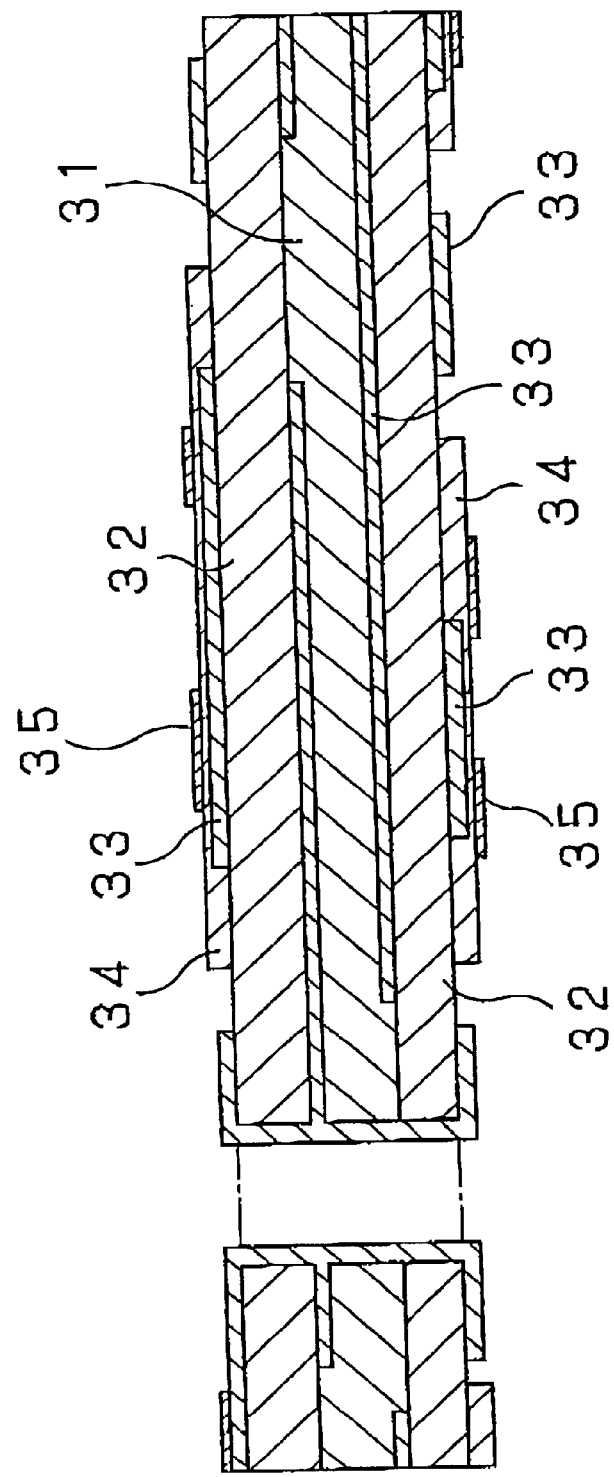
FIG. 3 is a sectional view of essential parts showing a different embodiment of a printed wiring board of the invention.

FIG. 3 shows essential parts in a different embodiment of the invention. FIG. 3 shows a four-layer copper through-hole printed wiring board. In FIG. 3, reference numeral 31 is a glass-epoxy (FR-4) insulating layer (inner layer substrate). Reference numeral 32 is an electronic component material containing cockroach repellent. This electronic component material containing cockroach repellent 32 is an insulating layer formed by pressing and curing a prepreg of glass-epoxy (FR-4) impregnating 100 parts by weight of principal ingredient epoxy rein and 80 parts by weight of this electronic component material containing cockroach repellent 32, in a glass fiber woven fabric. Reference numeral 33 is a conductive layer having a 25 μm copper plating applied on an 18 μm thick copper foil. Reference numeral 34 is a solder resist for exposure development of dual curing (ultraviolet curing+thermosetting) type. Reference numeral 35 is a thermosetting road map (parts layout).

Using the printed wiring boards in these three embodiments, after execution of heat load of high temperature and further execution of cleaning process, the cockroach repelling performance was evaluated, of which results are shown in Table 1. In a vinyl chloride vat of 80×100 cm, German cockroaches were placed, a paper shelter (nest) and a container of drinking water were put in the center, and reference pieces (conventional printed wiring boards) and test pieces (printed circuit boards of embodiments) were put at four corners of the vat. The conditions of heat load process and cleaning process are described in detail below.

Two hundred German cockroaches of each sex were used. Reference pieces and test pieces were specimens cut in 10 cm square. In the center of each one of the reference pieces and test pieces, cube sugar was placed, and the weight loss of cube sugar was measured 48 hours later, and the repelling rate (see below) was calculated. (Cockroaches are significant in heat attraction, and preferably it is should be evaluated by the heat attraction, but herein for the purpose of quantitative evaluation, the diet attraction was evaluated.)

Repelling rate=100×(control cube sugar weight loss−sample cube sugar weight loss)/control cube sugar weight loss [%]

As the reference pieces, in each constitution, samples not composing the electronic component material containing cockroach repellent were used.

The following results were obtained from Table 1.

The printed wiring boards of the embodiments present better cockroach repelling performances than the conventional printed wiring boards.

TABLE 1

| Reference piece: test piece | Cube sugar weight loss at reference piece side | | Cube sugar weight loss at test piece side | | Repelling rate |
|---|---|---|---|---|---|
| Conventional composition: composition in FIG. 1 | | 287.8 (mg) | | 23.8 (mg) | 90.6 (%) |
| | | 299.2 | | 31.5 | |
| | Mean | 293.5 | Mean | 27.7 | |
| Conventional composition: composition in FIG. 2 | | 278.3 (mg) | | 27.0 (mg) | 89.5 (%) |
| | | 301.4 | | 33.9 | |
| | Mean | 289.9 | Mean | 30.5 | |
| Conventional composition: composition in FIG. 3 | | 263.1 (mg) | | 50.9 (mg) | 82.2 (%) |
| | | 272.7 | | 44.5 | |
| | Mean | 267.9 | Mean | 44.7 | |

Further, as reference examples, using silicone resin instead of epoxy resin, printed wiring boards were fabricated in the same manner, and the sugar weight loss was about 90 to 250 mg. Also using urethane resin instead of epoxy resin, printed wiring boards were fabricated in the same manner, and the sugar weight loss was about 110 to 280 mg, and by executing the heat load process and cleaning process, the shape of the pest repelling layer was deformed. That is, the printed wiring boards of the embodiments produce extremely excellent cockroach repelling effects as compared with the composition of using the pest repellent of the prior art.

The adhesion of the electronic component material containing cockroach repellent to the printed wiring board is described below.

As shown below, three types of paste containing cockroach repellent were prepared, that is, ultraviolet curing type paste, thermosetting type paste, and dual curing type paste.

(a) An ultraviolet curing type paste containing 100 parts by weight of principal ingredient epoxy acrylate, reactive diluent, light initiator, filler, and pyrethroid derivative cockroach repellent (90 parts by weight, 100 parts by weight, 110 parts by weight), (b) A thermosetting type paste containing 100 parts by weight of principal ingredient epoxy resin, hardener, reaction promoter, filler, and pyrethroid derivative cockroach repellent (140 parts by weight, 150 parts by weight, 160 parts by weight), and (c) A dual curing type paste containing pyrethroid derivative cockroach repellent (90 parts by weight, 100 parts by weight, 110 parts by weight) in 100 parts by weight of principal ingredient epoxy resin, in a paste for exposure development of dual curing (ultraviolet curing+thermosetting) type composed of 100 parts by weight of principal ingredient epoxy resin, reactive diluent, light initiator, hardener, reaction promoter, coloring pigment, solvent, filler, and others.

Using these samples, after installing in the solder resist of the printed wiring board, heat load process (heat process of solder reflow and solder flow) and cleaning process in manufacture of electronic appliance were executed. Then, the adhesion of these samples was evaluated. The adhesion was evaluated according to the tape test of Japanese Industrial Standard C-5012. Results are shown in Table 2.

The following facts are known from Table 2.

An excel lent adhesion is obtained at the content of the cockroach repellent in the ultraviolet curing type paste of less than 110 parts by weight.

An excellent adhesion is obtained at the content of the cockroach repellent in the thermosetting type paste of less than 160 parts by weight.

An excellent adhesion is obtained at the content of the cockroach repellent in the dual curing type paste of less than 110 parts by weight.

As reference examples, pastes containing 90 parts by weight of cockroach repellent and not containing filler were prepared, and using these pastes, printed wiring boards were manufactured by disposing the same pest repelling layer as above, and the adhesion was tested. As a result, peeling of 85/100 or less was noted in the tape test.

As different reference examples, using a silicone resin of cold setting type, instead of the epoxy resin, pastes containing 90 parts by weight of cockroach repellent were prepared, and printed wiring boards were manufactured by disposing the same pest repelling layer as above, and the adhesion was tested. As a result, peeling of 80/100 or less was noted in the tape test.

As further reference examples, using a urethane resin of cold setting type, instead of the epoxy resin, pastes containing 90 parts by weight of cockroach repellent and not filler were prepared, and printed wiring boards were manufactured by disposing the same pest repelling layer as above, and the adhesion was tested. As a result, peeling of 85/100 or less was noted in the test.

TABLE 2

| Paste curing type | Cockroach repellent content | Tape test result | Judgement |
|---|---|---|---|
| Ultraviolet curing type | 90 parts by weight | 100/100 | ○ |
| | 100 parts by weight | 100/100 | ○ |
| | 110 parts by weight | 93/100 | X |
| Thermosetting type | 140 parts by weight | 100/100 | ○ |
| | 150 parts by weight | 100/100 | ○ |
| | 160 parts by weight | 98/100 | X |
| Dual curing type | 90 parts by weight | 100/100 | ○ |
| | 100 parts by weight | 100/100 | ○ |
| | 110 parts by weight | 89/100 | X |

* Cockroach repellent content is based on 100 parts by weight of principal ingredient resin.
○- Excellent Adhesion
X - Inferior Adhesion Explained below is the adhesion of the electronic component material using the following kinds of solder resist containing cockroach repellent.

(a) an ultraviolet curing type solder resist containing 100 parts by weight of principal ingredient epoxy acrylate, reactive diluent, light initiator, coloring pigment, filler, and pyrethroid derivative cockroach repellent (75 parts by weight, 80 parts y weight, 85 parts by weight), (b) A thermosetting type solder resist containing 100 parts by weight of principal ingredient epoxy resin, hardener, reaction promoter, coloring pigment, filler, and pyrethroid derivative cockroach repellent (110 parts by weight, 120 parts by weight, 130 parts by weight), and (c) A dual curing type solder resist (photo resist) containing 100 parts by weight of principal ingredient epoxy resin, reactive diluent, light initiator, hardener, reaction promoter, coloring pigment, filler, and pyrethroid derivative cockroach repel lent (75 parts by weight, 80 parts by weight, 85 parts by weight).

Using these samples, after installing in the copper foil and insulating substrate of the printed wiring board, heat load process (heat process of solder reflow and solder flow) in manufacture of electronic appliance was executed. Then, the adhesion of these samples was evaluated. Results are shown in Table 3.

The following facts are known from Table 3.

An excellent adhesion is obtained at the content of the cockroach repellent in the ultraviolet curing type solder resist of less than 85 parts by weight.

An excellent adhesion is obtained at the content of the cockroach repellent in the thermosetting type solder resist of less than 130 parts by weight.

An excellent adhesion is obtained at the content of the cockroach repellent in the dual curing type solder resist of less than 85 parts by weight.

TABLE 3

| | | Tape test result | | |
|---|---|---|---|---|
| Solder resist curing type | Cockroach repellent content | On conductive layer | On insulating layer of insulating board | Judgement |
| Ultraviolet curing type | 75 parts by weight | 100/100 | 100/100 | ○ |
| | 80 parts by weight | 100/100 | 100/100 | ○ |
| | 85 parts by weight | 91/100 | 97/100 | X |
| Thermosetting type | 110 parts by weight | 100/100 | 100/100 | ○ |
| | 120 parts by weight | 100/100 | 100/100 | ○ |
| | 130 parts by weight | 99/100 | 100/100 | X |
| Dual curing type | 75 parts by weight | 100/100 | 100/100 | ○ |
| | 80 parts by weight | 100/100 | 100/100 | ○ |
| | 85 parts by weight | 92/100 | 100/100 | X |

* Cockroach repellent content is based on 100 parts by weight of principal ingredient resin.

The adhesion of the electronic component material using a prepreg of glass-epoxy containing the repellent shown below is explained.

A prepreg impregnating 100 parts by weight of principal ingredient epoxy resin and pyrethroid derivative cockroach repellent (75 parts by weight, 80 parts by weight, 85 parts by weight) in a glass fiber woven fabric was pressed and cured in a copper foil of printed wiring board, and an insulating layer was formed. Using thus obtained laminate, heat load process (heat process of solder reflow and solder flow) was executed. The adhesion of thus obtained samples was evaluated. Table 4 summarizes the results of evaluation of adhesion (copper foil peeling strength). The testing method of peeling strength of copper foil used in adhesion evaluation conforms to Japanese Industrial Standard C-6481. The thickness of copper foil for test was 0.018 mm. The following results were obtained from Table 4.

An excellent adhesion was obtained at the content of the cockroach repellent in the prepreg of less than 85 parts by weight.

TABLE 4

| Cockroach repellent content | Peeling strength | Judgement |
| --- | --- | --- |
| 75 parts by weight | 0.87 kN/m | ◯ |
| 80 parts by weight | 0.83 | ◯ |
| 85 parts by weight | 0.78 | X |

* Cockroach repellent content is based on 100 parts by weight of principal ingredient resin.

In the above fabrication of samples, the heat load was executed in the following process.

Solder reflow (using far infrared ray as heat source, with maximum reaching temperature of substrate surface of 240° C., and residence time of 200° C. or more of 45 sec) was executed twice, on face and back. Then solder flow (solder bath set temperature of 260° C., residence time of 5 sec) was, executed once. It was then cleaned by isopropyl alcohol.

In the process of heat load in manufacture of electronic appliance (heat process of solder reflow and solder flow) and cleaning with solvent (for example, isopropyl alcohol) for removing the flux used in mounting of component, part of the cockroach repellent applied on the printed wiring board is likely to drop out. Deterioration of cockroach repellent was not induced even after the process of two sessions (face and back) of solder reflow (using far infrared ray as heat source, with maximum reaching temperature of substrate surface of 240° C., and residence time of 200° C. or more of 45 sec), one session of solder flow (solder bath set temperature of 260° C., residence time of 5 sec), and cleaning by isopropyl alcohol.

However, in order to obtain a sufficient cockroach repelling performance, it is preferred that the process is free from cleaning by solvent. Or the solder reflow process is preferred to be only once.

It is also preferred to use the electronic component material containing the following cockroach repellent.

(a) An ultraviolet curing type paste containing 100 parts by weight of principal ingredient epoxy acrylate, reactive diluent, light initiator, filler, and pyrethroid derivative cockroach repellent by 2 parts by weight or more, (b) A thermosetting type paste containing 100 parts by weight of principal ingredient epoxy resin, hardener, reaction promoter, filler, and pyrethroid derivative cockroach repellent by 5 parts by weight or more, (c) A dual curing type paste containing 100 parts by weight of principal ingredient epoxy resin, reactive diluent, light initiator, hardener, reaction promoter, coloring pigment, solvent, filler, and pyrethroid derivative cockroach repellent by 5 parts by weight, (d) An ultraviolet curing type solder resist containing 100 parts by weight of principal ingredient epoxy acrylate, reactive diluent, light initiator, coloring pigment, filler, and pyrethroid derivative cockroach repellent by 5 parts by weight or more, (e) A thermosetting type solder resist containing 100 parts by weight of principal ingredient epoxy resin, hardener, reaction promoter, coloring pigment, filler, and pyrethroid derivative cockroach repel lent by 8 parts by weight or more, and (f) A dual curing type solder resist containing 100 parts by weight of principal ingredient epoxy resin, reactive diluent, light initiator, hardener, reaction promoter, coloring pigment, filler, and pyrethroid derivative cockroach repellent by 10 parts by weight or more.

If the content of the cockroach repellent in each electronic component material above is less than the specified content, the repelling rate in the evaluation of cockroach repelling performance is 70% or less.

Similarly, in order to keep the repelling rate of base material and electronic component of 70% or more, the specified content of the cockroach repellent is preferred.

The ultraviolet curing type paste and ultraviolet curing type solder resist containing the cockroach repellent are often cured with part of the cockroach repellent floating in the surface layer. On the other hand, the thermosetting type paste and thermosetting type solder resist are cured with the cockroach repellent dispersed in the solvent. Therefore, the ultraviolet curing type paste and solder resist exhibit better cockroach repelling performance at the smaller content of the cockroach repellent than in the thermosetting type paste and solder resist. However, in the curing process of the dual curing (ultraviolet curing+thermosetting) type paste and solder resist (photo resist), since the ultraviolet curing is executed first, the cockroach repellent is relatively dispersed in the surface layer. Therefore, the dual curing type paste and solder resist present the cockroach repelling performance similar to that of the ultraviolet curing type resist.

A manufacturing method of electronic component of the invention comprises the following steps.

(a) A step of manufacturing a printed wiring board by disposing a conductive layer having a mounting land on a substrate, (b) A step of preparing an electronic component material having a pest repellent and a resin which can be crosslinked, (c) A step of applying or disposing the electronic component material on a desired surface of the printed wiring board except for the mounting land, (d) A step of forming a pest repelling layer in contact with the printed wiring board, by crosslinking and chemical reaction of the resin in the electronic component material on the printed wiring board, (e) A step of soldering other electronic components on the mounting land of the printed wiring board on which the pest repelling layer is disposed, and (f) A step of cleaning the printed wiring board having the pest repelling layer and soldered other electronic components by an organic solvent.

In this method, as the electronic component material containing the pest repel lent, various electronic component materials as mentioned above can be used.

Furthermore, in the above steps, the following steps may be also included.

(g) A step of forming an insulating layer by solder resist or the like by covering the conductive layer, and applying, curing and drying the electronic component material containing the pest repellent on the surface of this insulating layer.

(h) A step of manufacturing the printed wiring board by pressing and heating by laminating a prepreg and a copper foil, in which the electronic component material is a prepreg impregnating the pest repellent and resin in glass-epoxy, and the conductive layer is a copper foil.

The electronic component manufactured in this method has the same effects as the above electronic components. Moreover, the pest repelling layer formed in this method has the functions of both pest repelling performance and electric insulating layer.

In the electronic component material, electronic component, and manufacturing method of electronic component of the invention thus explained, the resin which can be crosslinked and cured is preferably a resin containing an epoxy group in its chemical structure. As the resin containing epoxy group, prepolymer and epoxy acrylate having plural epoxy group are particularly preferred.

By chemical reaction between the prepolymer having plural epoxy groups and hardener, a crosslinked cured resin is formed. The reactive diluent is a liquid having a small viscosity which can react by crosslinking. As the reactive diluent of epoxy resin, for example, glycidyl alcohol is used. Usable examples of hardener include organic acid, acid anhydride, organic amine, organic imide, and others that can react with the epoxy group. The hardening promoter includes organic amine and organic imide, among others. The content of the hardener should be equivalent to the sum of epoxy groups in the epoxy resin and reactive diluent. The content of the reactive promoter is about 0.1 to 5 parts by weight of the epoxy resin. A mixture of the epoxy resin, reactive diluent, hardener, and curing promoter is cured and dried by the crosslinking reaction by heating. The solvent is evaporated at this time of crosslinking reaction.

The epoxy acrylate is a prepolymer having both epoxy group and plural acrylic groups in chemical structure, or a prepolymer having an acrylic group and plural epoxy groups. The reactive diluent is a liquid monomer having both epoxy group and acrylic group, or a liquid monomer having a double bond in its chemical structure. The monomer having both epoxy group and acrylic group includes, for example, glycidyl acrylate and glycidyl methacrylate. Examples of monomer having double bond include alkyl methacrylate, alkyl acrylate, and styrene compound. The light initiator generates an active group when irradiated with ultraviolet rays or other beams of light. The mixture of such epoxy acrylate, light initiator, and reaction diluent is cured and dried by crosslinking reaction when exposed by beams of light. Crosslinking reaction is induced by reaction of double bond of acrylate group.

The mixture of epoxy resin, epoxy acrylate, hardener, and light initiator is exposed by means of light, and double bond reacts by crosslinking, and the epoxy resin and hardener react by crosslinking by heating.

The pest repellent and filler added to the mixture of such resin are dispersed and contained in the hardened matter. Further, if the viscosity of the paste and solder resist of the mixture is low, in the crosslinking reaction process, part of the pest repellent is contained in a state flowing on the surface of the pest repelling layer.

As the solvent, for example, a compatible liquid such as curable resin, hardener and light initiator may be used. As the solvent, more particular, a liquid capable of dissolving the pest repellent is preferred. When the paste, solder resist or prepreg reacts by crosslinking, the solvent- dissolving the pest repellent is evaporated, and part of the pest repellent is exposed to the surface.

When the electronic component material having the resin with epoxy group and pest repellent is cured in contact with a base material, the cured pest repelling layer has an extremely strong adhesion to the base material. Moreover, the cured pest repelling layer has a high heat resisting property to withstand high temperature in heat load process. Furthermore, the cured pest repelling layer does not deteriorate if immersed in the solvent in the cleaning process after soldering. The cured pest repelling layer has the function of excellent electric insulating layer, and hence when used as the electric insulating layer of the conductive layer of printed wiring board, the number of steps of manufacturing is curtailed, and the manufacturing cost is lowered.

In such constitution, the electronic component such as printed wiring board for composing an electronic appliance itself has the cockroach repelling performance. Or, the insulating layer itself has the cockroach repelling performance. In this constitution, invasion and staying of cockroaches are suppressed, troubles of electronic appliances due to dead bodies and excrement of cockroaches are prevented, and the reliability is enhanced. At the same time, adverse effects on the human can be decreased. It is also possible to apply the electronic component material containing the repellent of the invention in the enclosure or furnace (cables) used in the electronic appliance, so that the more secure cockroach repelling performance is achieved in this constitution.

Furthermore, in the high temperature heat load process or cleaning process, deterioration of cockroach and other pest repelling performance does not occur, and an excellent pest repelling performance is maintained. In addition, the adhesion between the pest repelling layer and substrate is extremely enhanced.

In the embodiments, the cockroach repellent is contained, but, instead, electronic component materials containing other pest repellents may be also realized, and the same effects as above are exhibited. As the cockroach repellent, instead of the pyrethroid derivative repellent, other cockroach repellents may be used, and the same effects can be obtained. In particular, by containing the cockroach repellent in the thermosetting paste or thermosetting solder resist, the reliability of electronic components such as printed wiring boards can be easily assured.

Still more, by composing the component by using the resist and paste containing neurotransmitter repellent making use of skin stimulation of antennae or the like of pest insects, the reliability of the electronic appliances may be assured also in ants and other pest insects obtaining the same activity information by antennae and others as in cockroaches. At the same time, effects on the human can be decreased.

What is claimed is:

1. A method of manufacturing an electronic component having a pest repelling layer for repelling pest insects from the surface of a printed wiring board,
    (a) preparing an electronic component material having a pest repellent and a resin which may be crosslinked and cured,
    (b) applying said electronic component material at a specified position on the surface of said printed wiring board,
    (c) forming said cured pest repelling layer, containing said pest repellent, by crosslinking chemical reaction of said resin in said electronic component material on said printed wiring board, said pest repellent having a pyrolysis temperature of greater than about 250° C., wherein said electronic component material is a prepreg containing said resin and said pest repellent impregnated in a glass woven fabric or in a glass non-woven fabric, and curing the resin by heating and pressing, and when said resin is cured, said pest repelling layer is formed in a state in which part of said pest repellent is moved to the surface of said pest repelling layer by the action of a reactive diluent.

2. A method of manufacturing an electronic component having a pest repelling layer for repelling pest insects from the surface of a printed wiring board, (a) preparing an electronic component material having a pest repellent and a resin which may be crosslinked and cured, (b) applying said electronic component material at a specified position on the surface of said printed wiring board, (c) forming said cured pest repelling layer, containing said pest repellent, by crosslinking chemical reaction of said resin in said electronic component material on said printed wiring board, said pest repellent having a pyrolysis temperature of greater than about 250° C., wherein said electronic component material is a prepreg containing said resin and said pest repellent impregnated in glass woven fabric or in a glass non-woven fabric, said printed wiring board has a glass-epoxy electric insulating board and a copper clad circuit, and pressing and heating the glass-epoxy prepreg, said copper clad circuit, and said electronic component material, and laminating and forming said electric insulating board, said copper clad circuit, and said pest repelling layer.

3. A method of manufacturing an electronic component having a pest repelling layer for repelling pest insects from the surface of a printed wiring board, (a) preparing an electronic component material having a pest repellent and a resin which may be crosslinked and cured, (b) applying said electronic component material at a specified position on the surface of said printed wiring board, (c) forming said cured pest repelling layer, containing said pest repellent, by crosslinking chemical reaction of said resin in said electronic component material on said printed wiring board, said pest repellent having a pyrolysis temperature of greater than about 250° C., wherein said electronic component material is a prepreg containing said resin and said pest repellent impregnated in a glass fabric.

4. A method of manufacturing an electronic component having a pest repelling layer with a function of repelling pest insects on the surface of a printed wiring board, said method comprises the steps of:

(a) preparing an electronic component material having a pest repellent and a resin, said electronic component material having said resin and said pest repellent impregnated into a glass fabric, (b) applying said electronic component material at a specified position on the surface of said printed wiring board, and (c) laminating said electronic component material and said printed wiring board with heat and pressure.

5. The method of manufacturing an electrnic component of claim 4, wherein said resin is a crosslinkable resin, and said pest repelling layer is formed by a crosslinking chemical reaction forming a crosslinked resin.

6. The method of manufacturing an electronic component of claim 4, wherein said pest repellent has pyrolysis temperature of greater then about 250° C.

7. The method of manufacturing electronic component of claim 4, wherein said pest repellent includes a pyrethroid pesticide having pyrolysis temperature of greater than about 250° C.

* * * * *